United States Patent [19]

Telikicherla

[11] Patent Number: 5,651,792
[45] Date of Patent: *Jul. 29, 1997

[54] FLEXIBLE LOWER LIMB PROSTHETIC ASSEMBLY WITH REMOVABLE DRESSING

[76] Inventor: Madan M. Telikicherla, 4293 Margate La., Bloomfield Hills, Mich. 48013

[*] Notice: The term of this patent shall not extend beyond the expiration date of Pat. No. 5,108,455.

[21] Appl. No.: 318,880

[22] PCT Filed: Apr. 27, 1992

[86] PCT No.: PCT/US92/03438

§ 371 Date: Oct. 18, 1994

§ 102(e) Date: Oct. 18, 1994

[87] PCT Pub. No.: WO93/21865

PCT Pub. Date: Nov. 11, 1993

Related U.S. Application Data

[63] Continuation-in-part of Ser. No. 408,884, Sep. 18, 1989, Pat. No. 5,108,455, which is a continuation-in-part of Ser. No. 260,617, Oct. 21, 1988, abandoned.

[51] Int. Cl.$^6$ .................... A61F 2/62; A61F 2/78
[52] U.S. Cl. .................... 623/36; 623/38; 602/63
[58] Field of Search .................... 623/32–43, 53, 623/55; 602/62, 63, 65, 23–25

[56] References Cited

U.S. PATENT DOCUMENTS

| | | |
|---|---|---|
| 912,130 | 2/1909 | James . |
| 1,071,149 | 8/1913 | Erickson . |
| 1,082,256 | 12/1913 | Apgar . |
| 2,464,443 | 11/1949 | Ganoe et al. . |
| 2,500,622 | 3/1950 | Aho . |
| 3,043,297 | 7/1962 | Curnin . |
| 3,707,731 | 1/1973 | Morgan . |

(List continued on next page.)

FOREIGN PATENT DOCUMENTS 2 103 490  2/1983  United Kingdom .

OTHER PUBLICATIONS

Burgess et al., "Immediate Post-Surgical Prosthetics", *Orthopedic & Prosthetic Appliance Journal*, 1967, pp. 105–112; presented at 1966 Assembly of the American Orthotic and Prosthetic Association, Palm Springs, CA.

Golbranson et al., "Immediate Postsurgical Fitting and Early Ambulation", *Clinical Orthopaedics and Related Research*; 119–131.

(List continued on next page.)

*Primary Examiner*—David H. Willse
*Attorney, Agent, or Firm*—Spencer & Frank

[57] ABSTRACT

A lower limb prosthetic assembly for immediate post-operative amputation applications includes a temporary weight-bearing prosthetic device and an independent removable, replaceable, size-adjustable dressing adapted for immediate post-operative placement around the patient's amputation stump. The temporary weight-bearing prosthetic device includes an adjustable support member, and an open ended quadrilateral thigh socket having a padded ischial weight-bearing shelf for supporting the patient without contact to the stump wound. The dressing provides mild, uniform circumferential pressure to the amputation stump and suppresses edema of the stump. The dressing is dimensioned to leave the portion of the gluteus maximus over the ischial tuberosity free for engagement with and support by the ischial shelf of the prosthetic device. The support member includes lockable knee joints, and a cable release for unlocking the knee joints. For knee disarticulation or below knee amputation applications, the temporary prosthetic device includes a knee pad and a back panel between the medial and lateral uprights, in order to prevent the stump from moving dorsally ("flopping") with respect to the device. The invention thus provides a prosthetic assembly which is prefabricated, adjustable, economical and easy to use, one which can be used as early as a few hours after the amputation operation.

52 Claims, 7 Drawing Sheets

U.S. PATENT DOCUMENTS

| | | | |
|---|---|---|---|
| 3,844,279 | 10/1974 | Konvalin | 602/23 X |
| 4,100,918 | 7/1978 | Glancy | 602/16 |
| 4,128,903 | 12/1978 | Marsh et al. | |
| 4,161,042 | 7/1979 | Cottingham et al. | |
| 4,268,922 | 5/1981 | Marsh et al. | |
| 4,274,166 | 6/1981 | Chambers | |
| 4,634,446 | 1/1987 | Kristinsson | |
| 4,842,608 | 6/1989 | Marx et al. | |
| 4,872,879 | 10/1989 | Shamp | |
| 5,108,455 | 4/1992 | Telikicherla | |
| 5,342,288 | 8/1994 | Lee et al. | 602/5 |

OTHER PUBLICATIONS

Burgess, Ernest et al., "The Management of Lower Extremity Amputees Using Immediate Postsurgical Prostheses"; *Clinical Orthopaedics and Related Research*; pp. 137–146.

Bonner, et al, "Pneumatic Airleg Prosthesis: Report of 200 Cases", ArchPhyMedRehabil, vol. 63, Aug. 1982; pp. 383–385.

Monga et al, "Load bearing and suspension characteristics of airsplint as a temporary prosthesis", *Prosthetics and Orthotics International*, 1985, pp. 100–104.

Nicholas et al., "Evaluation of Use of the Rigid Dressing in Amputation of the Lower Extremity"; From the Dept of Surgery, The Milton S. Hershey Medical Center of the Penn State University, Hershey; pp. 398–400.

Kane et al, "The Rigid Versus Soft Postoperative Dressing Controversey: A Controlled Study in Vascular Below–Knee Amputees" From the Dept. of Surgery, Univ. of Cal., Davis, CA and Univ. of Missouri, Kansas City, MO, p. 244.

Devas, M.B., "Early Walking or Geriatric Amputees" *British Medical Journal*, 1971, I, pp. 394–396.

Ghiulamila, R.I.; "Semirigid Dressing for Postoperative Fitting of Below–Knee Prosthesis"; Archives of Physical Medicine & Rehabilitation, pp. 186–190.

Jeffery, A.K., "Below–knee Amputation and Immediate Prosthetic Fitting in Vascular Disease", *New Zealand Medical Journal*, Oct. 23, 1974, pp. 343–349.

Little et al., "Experience with a Pneumatic Lower–Limb Prosthesis", *The Medical Journal of Australia*, Jun. 17, 1972; pp. 1300–1303.

Sarmiento et al., "Immediate Postoperative Fitting of Below–knee Amputations", Physical Therapy, vol. 50, No. 1, Jan. 1970, pp. 10–19.

Barraclough et al., "Air Splints Used as Immediate Post–Operative Prostheses After Long Posterior Flap Below–knee Amputation"; *The Medical Journal of Australia*; Sep. 30, 1972; pp. 764–767.

Russek et al., "Ischial Weight Bearing Brace with Quadrilateral Wood Top–Preliminary Report", *Orthopedic & Prosthetic Appliance Journal*, Sep. 1958, pp. 31–35.

Wu et al., "An Innovative Removable Rigid Dressing Technique for Below–the–Knee Amputation", *The Journal of Bone and Joint Surgery*, vol. 61–A, No. 5, Jul. 1979, pp. 724–729.

*Atlas of limb prosthetics*, Surgical and Prosthetic Principles, American Academy of Orthopaedic Surgeons, The C.V. Mosby Company, 1981, p. 52.

Dickstein, R. et al., "Use of the Early Walking Aid as a 'Geriatric Prothesis' in the Community"; *Journal of Prosthetics and Orthotics*, vol. 1, No. 2, pp. 110–115.

Redhead, R.G., "The early rehabilitation of lower limb amputees using a pneumatic walking aid", *Prosthetics and Orthotics International*, 1983, 7, pp. 88–90.

Devas, M., "The Geriatric Amputee", *Geriatric Orthopaedics*, Academic Press, 1977.

Lehmann, J., et al., "Biomechanical Evaluation of Axial Loading in Ischial Weight–Bearing Braces of Various Designs", *Archives of Physical Medicine & Rehabilitation*, Jun. 1970, pp. 331–337.

Grynbaum, B. et al., "An Adjustable Ischial Weight–Bearing Brace for Early Ambulation in Lower Extremity Fractures", *Arch Phys Med Rehabil* vol. 54, 1973, pp. 556–668.

Lehmann, J. et al, "Trends in Lower Extremity Bracing", Archives of Physical Medicine & Rehabilitation, Jun. 1970, pp. 338–353.

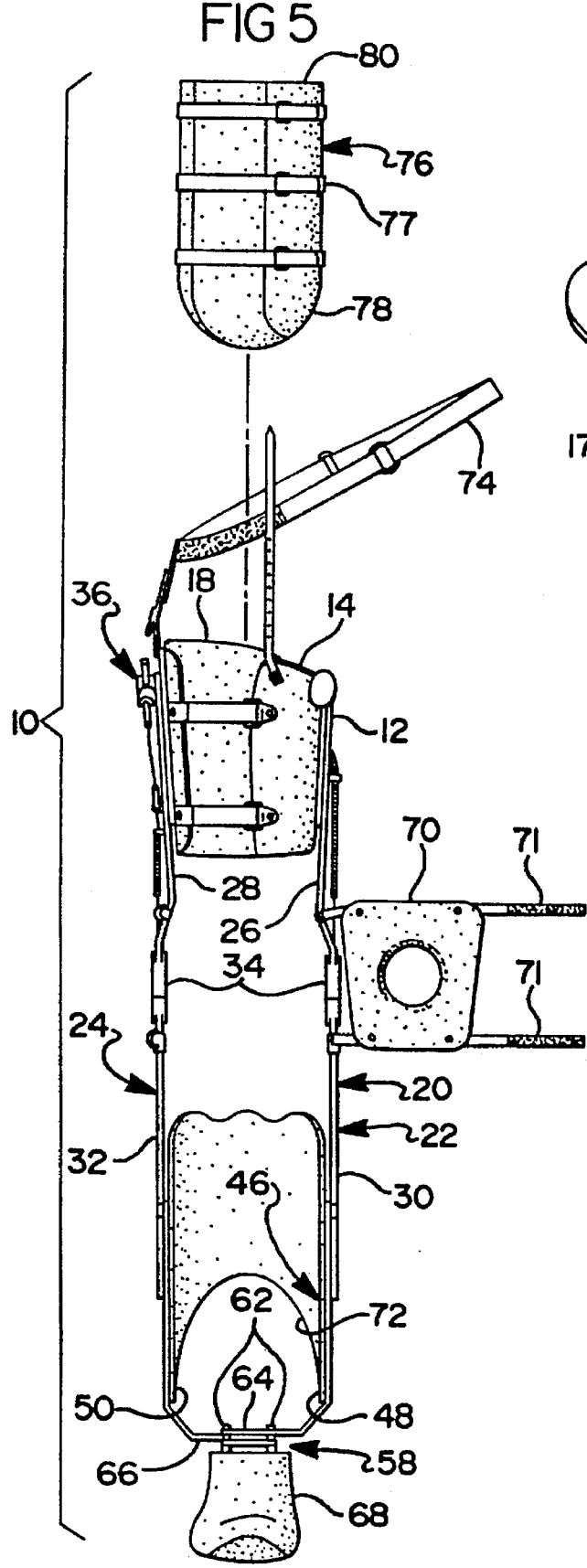
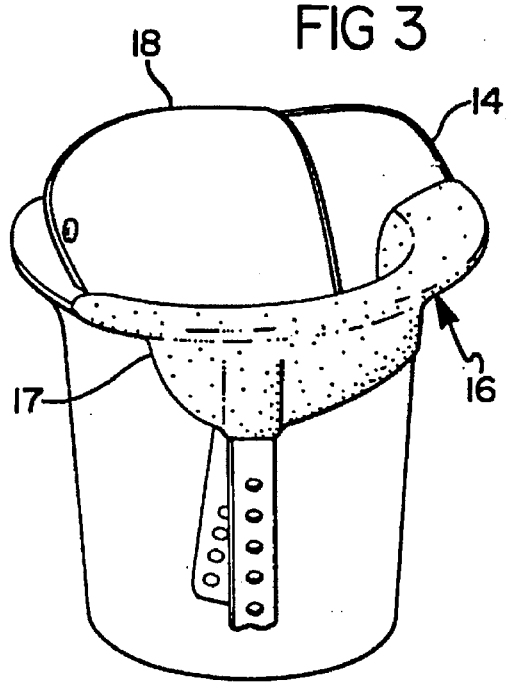
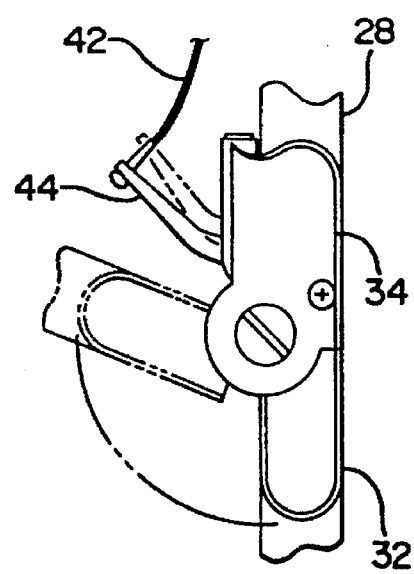

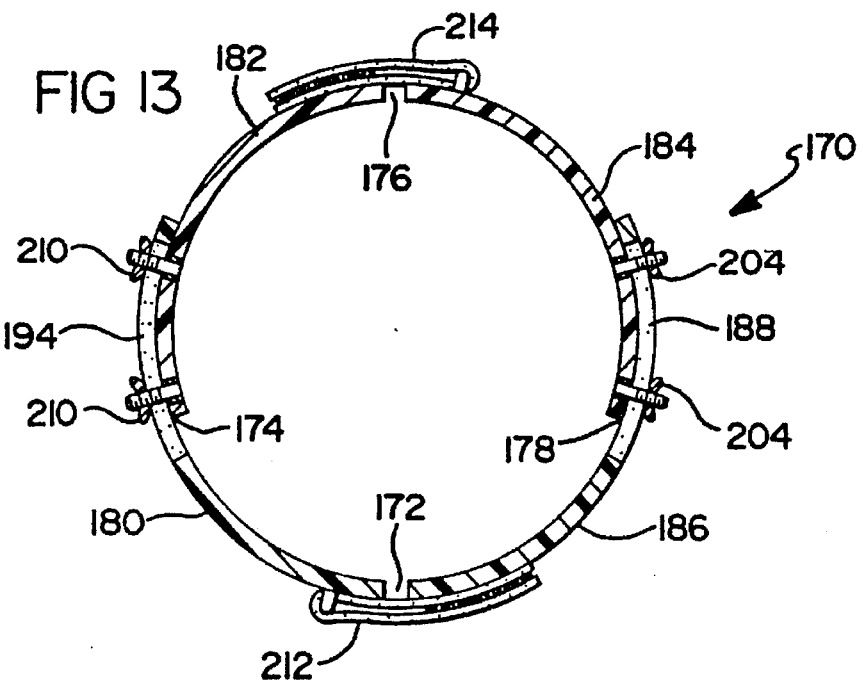
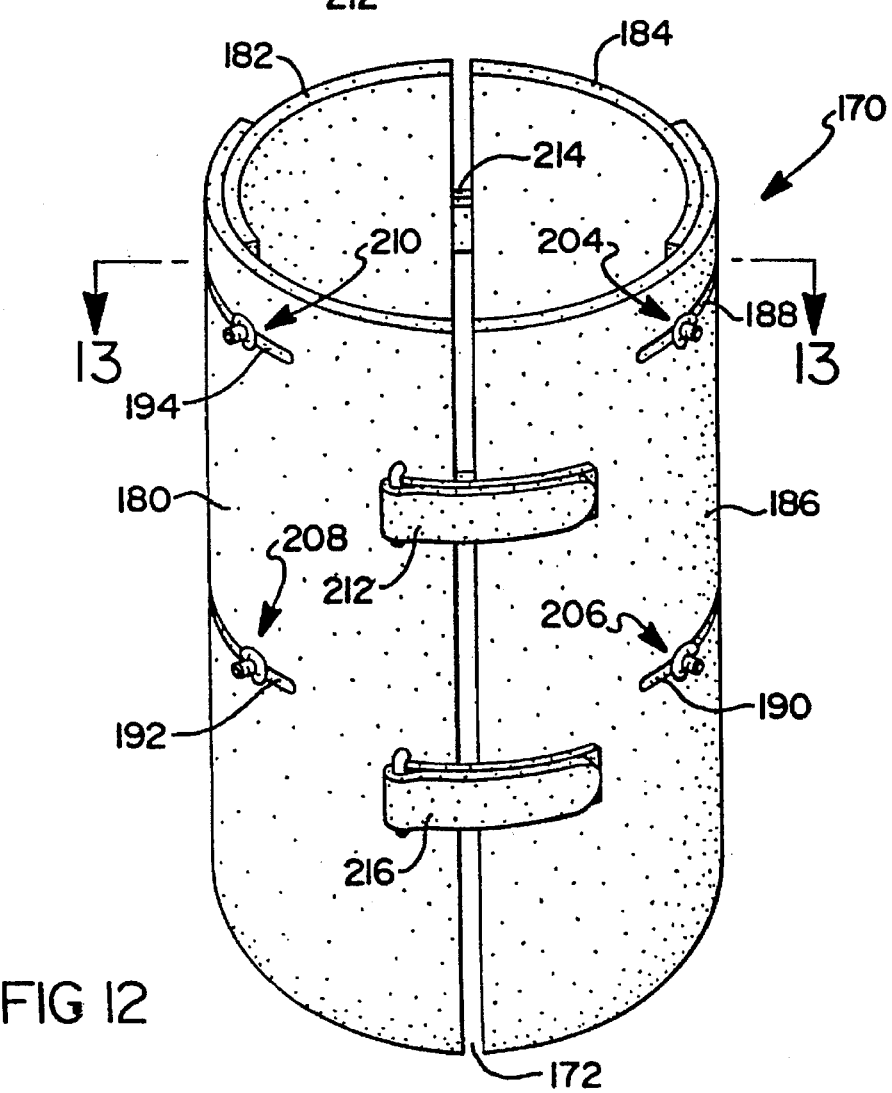

FLEXIBLE LOWER LIMB PROSTHETIC ASSEMBLY WITH REMOVABLE DRESSING

CROSS REFERENCE TO RELATED APPLICATIONS

This application is a continuation-in-part of Applicant's U.S. patent application Ser. No. 5 408,884, filed on Sep. 18, 1989 (U.S. Pat. No. 5,108,455, issued Apr. 28, 1992). That application was in turn a continuation-in-part of Applicant's then U.S. patent application Ser. No. 260,617, filed on Oct. 21, 1988, and now abandoned. application Ser. No. 408,884 is expressly incorporated by reference herein.

TECHNICAL FIELD

The present invention relates to rehabilitative devices especially suitable for amputated limbs, and more particularly to a lower limb prosthetic assembly for immediate post-operative application in above knee amputations, below knee amputation and knee disarticulations.

BACKGROUND OF THE INVENTION

The loss of a lower extremity, even by careful surgical amputation, has profound physical and psychological consequences to the patient. It has long been known to remedy some of these consequences by providing a permanent prosthetic device to restore to the patient part of the function once performed by the lost limb. It is now generally accepted, however, that early post-operative weight bearing may be extremely valuable in both the physical and psychological rehabilitation of the amputee. By resuming ambulation with partial or full weight-bearing at an early stage, postural reflexes can be maintained, even while the residual stump is healing and being readied for a definitive fitting of a permanent prosthetic device.

Many advantages are offered by fitting a prosthetic device immediately after amputation. These include early ambulation, more rapid healing of the amputation site, decreased post-operative pain and edema of the stump, shorter hospitalization times, earlier fitting of a definitive prosthesis and a general improvement of the physical condition of the patient by preventing hypostatic pneumonia, phlebothrombosis, disuse weakness and psychological depression. The immediate post-operative prosthetic device thus aids the amputation team (consisting of the surgeon, the physiatrist, the prosthetist and the physical therapist) in the efficient treatment of the amputee.

Until recently, the amputation site was treated post-operatively with disposable soft compressive dressings, non-removable rigid dressings, or with so-called removable rigid dressings made from a plaster or fiberglass cast. These last were considered "removable" because they could be pulled off of the stump and then replaced upon it after inspection of the stump.

Both the removable and non-removable rigid dressings permitted partial or full weight-bearing through a temporary prothesis until the amputation wound had healed. For example, some rigid dressings served as prostheses sockets to which temporary prosthetic supports were attached. Such constructions were disadvantageous, however, in that they required that the full weight of the patient be borne on the amputation stump, interfering with patient healing and making it painful for the patient to use the prosthetic device. This was true even of pneumatic dressings; while soft and removable, they were still used in conjunction with rigid sockets, and so put the full weight of the patient on the stump.

Moreover, prior prostheses formed by embedding supports in rigid dressings were unitary and inflexible, making them difficult for patients to use. A prosthetic device which is painful or difficult to use does not get used at all, to the detriment of the patient.

The prior rigid dressings had other drawbacks. For example, to allow inspection of the amputation wound, the so-called removable rigid dressings were merely pulled off the amputation stump, causing very great pain to the patient and generating so much friction as to traumatize the amputation wound and the skin of the stump. Even when a felt pad was positioned between the stump and the rigid cast, the intense pain of removal and replacement discouraged patients from having their wounds inspected daily. Daily inspection, of course, is an indispensable part of proper amputation patient care.

Another drawback arose from the fact that removable rigid dressings were generally applied immediately after the amputation operations, while the patients were still on the operating table. Application of plaster cast or glass fiber dressings detrimentally affected patients because of the great amount of heat evolved during the curing of the casts. The problem was of particular concern because residual limbs already experience compromised circulation, especially when amputations are performed for peripheral vascular disease.

Another drawback arose in the casting method for making rigid dressings. By their very nature, the casts of the rigid dressings were custom made, tediously fitted to the dimensions of a particular patient's stump at the time of the amputation operation. Such cast were not subject to reuse or adjustment, and required frequent replacement when stump dimensions changed, as the stump cured and the swelling of the stump decreased.

Yet another drawback to the use of rigid casts as post-operative dressings was the extensive expertise required for their proper application. Techniques of this type were available to patients only at special medical centers where experienced prosthetists were available. Proper technique was critical because localized pressure areas from wrinkles or faulty plastering technique could cause pressure sores or decubitus ulcers, delaying healing of the amputation wound or resulting in infection of the wound. Moreover, even though plaster casts with rigid support posts didn't provide for full weight bearing, alignment of the support on the stump was still very difficult.

Of course, since the rigid casts generally did not allow inspection of the amputation site on a daily basis, a high incidence of stump complications was possible, requiring even more frequent removal and replacement of the rigid cast. The patient was thus obligated to return to the special medical center on a repeated and continuing basis, until such time as a definitive prosthetic device could be fitted.

My copending U.S. patent application Ser. No. 408,884, filed Sep. 18, 1989, contains a more extensive historical background to these problems and is incorporated by reference herein. That application was directed to a removable, size-adjustable rigid dressing for placement around a patient's amputation stump, and a lower limb prosthetic assembly incorporating such a dressing, and solved many of the drawbacks noted above. However, my prior device was perhaps not as conducive to post-operative ambulation as might be desired. It is critical to the success of an immediate post-operative prosthetic assembly that it be comfortable and convenient to use; a prosthetic device that pains the patient or is a struggle to use will not be used at all, and the patient will fail to gain the benefit of the device. It would be desirable to make my earlier assembly and dressing easier to adjust and fit to a particular patient; to restrict the limb stump flop sometimes encountered with the use of the assembly; to provide an easier control over locking of the knee joints of the assembly; and to make the assembly and dressing more comfortable to use and reduce the chance of impairment of circulation at the ischial cleft of the patient using the device.

Accordingly, it is an object of the present invention to provide a cost effective, easy-to-fit prosthetic assembly which is prefabricated and adjustable to the different height and orientation requirements of individual patients.

It is also an object of the present invention to provide a prosthetic assembly useful with a variety of amputation stumps yet which allows full weight-bearing within the first few hours or days after the amputation surgery, obviating any weight-bearing on painful and swollen amputation stumps, or on fresh or unhealed amputation wounds, without compromise of wound healing, skin integrity or circulation in the residual limb.

It is a further object of the present invention to provide a prosthetic assembly having an independent removable dressing, one whose ease of application obviates the need for the extreme degree of training required for the application of prior rigid cast dressings, but which in use achieves full ischial weight-bearing without compromising healing of the amputation wound.

SUMMARY OF THE INVENTION

In accordance with the present invention, there is provided an immediate post-operative prosthetic assembly useful for lower limb amputation applications, which comprises a temporary weight-bearing prosthetic device, and an independent removable, replaceable, size-adjustable dressing adapted for immediate post-operative placement around the patient's amputation stump, having means for providing mild uniform circumferential compression to the amputation stump and suppressing edema of the stump. The temporary weight-bearing device includes (a) an open-ended quadrilateral thigh socket having an ischial weight-bearing shelf for supporting the patient without contact to the amputation wound, (b) a support member attached to and extending from the quadrilateral thigh socket for supporting the patient, and (c) means for adjusting the length of the support member to a particular patient. The independent removable dressing is dimensioned to leave the portion of the gluteus maximus over the ischial tuberosity of the patient (the gluteal crease) free for engagement with and support by the ischial shelf of the temporary prosthetic device. To use the assembly, the patient simply sits on the prosthetic device, with the dressing passed through the socket, and the gluteal crease resting on the ischial shelf.

Preferably, the support member of the temporary device includes medial and lateral uprights, each having upper and lower portions joined by knee joints, and an endoskeletal shank attached to the lower portions of the medial and lateral uprights. Also preferably, the means for adjusting the length of the support member simultaneously serves to connect to the endoskeletal shank to the medial and lateral uprights, preferably to the lower portions of them.

In one related aspect, the temporary prosthetic device includes locks for the knee joints, and a manually operable cable release for the knee locks. Alternatively, each knee lock may be a drop lock, a bail lock, or other suitable locking mechanism for allowing cosmesis while sitting, and stability without knee buckling while standing. In another related aspect, a padded sleeve is provided on the ischial shelf of the quadrilateral thigh socket. In a third related aspect, particularly when the prosthetic assembly is intended for use with a patient having a below knee amputation, the temporary prosthetic device includes either or both of a dorsal knee pad connected to the medial and lateral uprights adjacent to the knee joints, and/or a back panel affixed to the lower portions of the medial and lateral uprights, in order to stop undesired movement (flopping) of the stump with respect to the temporary prosthetic device. In still another related aspect, a prosthetic foot assembly is affixed to the distal end of the endoskeletal shank, adjustable medially or laterally with respect to the uprights of the temporary prosthetic device.

The quadrilateral thigh socket of the temporary prosthetic device can be made of an orthoplast-type material, as well as other conventional thermoplastic or thermosetting materials. The ischial weight-bearing shelf is attached to the upper inner rear portion of the thigh socket and may be from about ½ inch to about 2 inches in width, from about 1 to about 4 inches in length, and from about ½ to about 1 inch deep, depending upon the intended application. The padded sleeve on the shelf may be composed of foam rubber or another resilient material and may have a thickness of from about ⅛ to about ½ inch, depending upon its composition.

With respect to the independent removable dressing, it can be used in conjunction with the temporary prosthetic device described above, thereby yielding the prosthetic assembly of the present invention, or it can be used apart from the device, thereby constituting an intimately related but patentable aspect by itself. As in my earlier application, the dressing can be rigid and can include both a means for adjusting the size of the dressing to an individual patient, and a locking means permitting separation and reconnection of fitted portions of the rigid dressing about the amputation stump. More particularly, the removable rigid dressing can comprise two or more longitudinally extending circumferential shells connectable by the locking means, each of the shell portions being adjustable in width, that is, in circumferential extent about the amputation stump. In the embodiments shown in my prior application, these longitudinally extending circumferential portions were described as vertical half shells.

As an alterative to this rigid dressing, the independent removable dressing of the present invention can be a soft dressing, that is, one lacking an outer shell or cast. In either the rigid or soft dressings, however, the dressing preferably comprises a pad, and the circumferential compressing means is disposed about the pad, for mildly and uniformly compressing the pad against the patient's amputation stump. The circumferential means can include the rigid shells described above, but in its simplest form, the circumferential means comprises at least one releasable strap circumferentially disposed about the pad. If present, the rigid shells are positioned between the pad and the circumferential straps.

The dressing pad preferably includes a generally cylindrical body and a hemispherical closed end. In one preferred embodiment, the pad has a plurality of laterally tapered, longitudinally extending petals formed by longitudinally extending and preferably arcuate cuts through the pad body and through part of the closed pad end. In another preferred embodiment, the pad body and the pad end are longitudinally split by a single longitudinally extending cut through the pad body and through part of the hemispherical pad end, extending in the hemispherical end to at least the axis of the cylindrical body. In this latter embodiment, at least one supplemental strap is included extending across the cut in the hemispherical pad end. In this manner, mild and uniform compression is also applied to the end of the stump, as well as about the circumference of the stump. Also in this latter embodiment, the circumferential means includes a fabric cover positioned between the pad and the circumferentially disposed strap or straps, the strap or straps being affixed to the cover, rather than to the pad.

Many of the construction and composition details of the other elements of the lower limb prosthetic assembly of the present invention are shown in my earlier application Ser. No. 408,884, and need not be repeated in the following detailed description of the invention, since incorporated by reference herein.

BRIEF DESCRIPTION OF THE DRAWING

Further objects and advantages of the present invention will be made more clear by the following detailed description, with reference to the accompanying drawing in which:

FIG. 3 is a perspective view of a quadrilateral thigh socket and ischial weight-bearing shelf of the thigh socket employed in the prosthetic assembly shown in FIG. 1;

FIG. 4 is a detailed view similar to FIG. 2 showing operation of the cable release for the knee joint lock;

FIG. 5 is a ventral or front view of a lower limb prosthetic assembly constructed in accordance With the present invention and particularly adapted for use with a patient having a below knee amputation;

FIG. 12 is a perspective view of another alterative dressing for incorporation in the prosthetic assembly of the present invention; and FIG. 13 is a cross-sectional view taken along line 13—13 of FIG. 12.

DETAILED DESCRIPTION OF THE INVENTION

Figure 1:
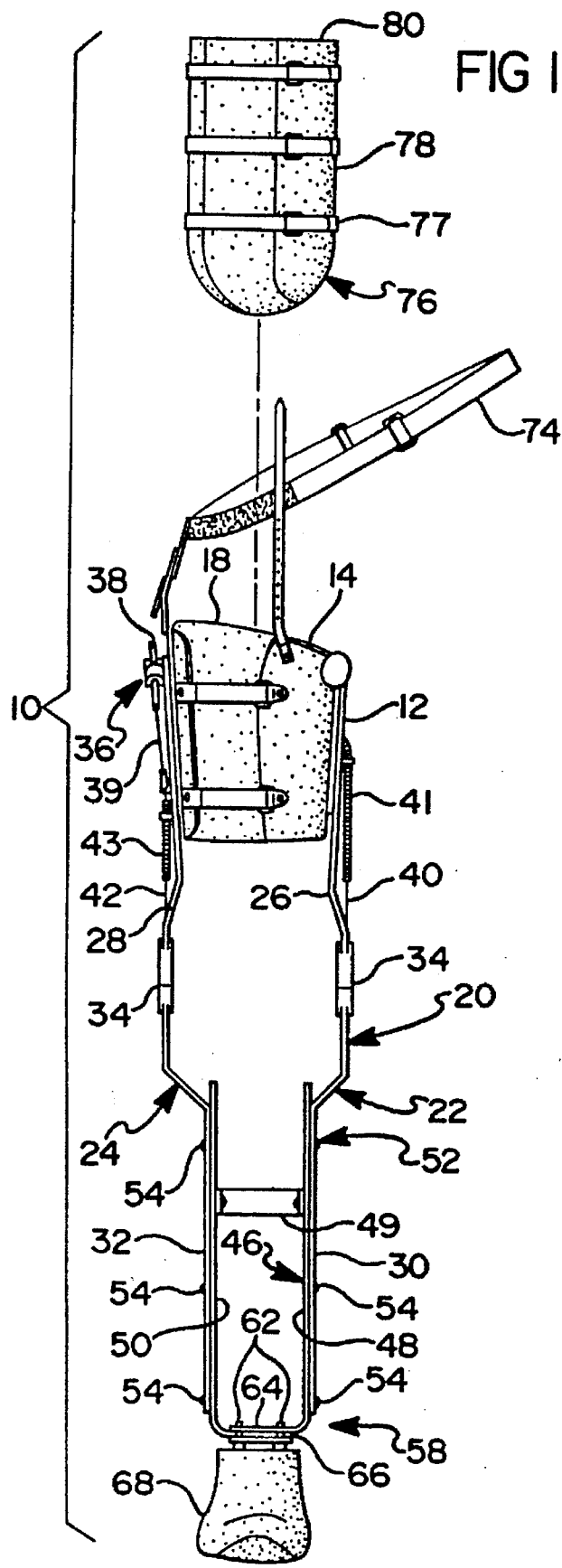
FIG. 1 is a front or ventral view of a lower limb prosthetic assembly in accordance with the present invention adapted for use on a patient having an amputation above the patient's right knee.

With reference first to FIG. 1, a lower limb prosthetic assembly 10 for immediate post-operative amputation applications is thereshown and first comprises a temporary weight-bearing prosthetic device 12. The prosthetic device 12 includes an open-ended quadrilateral thigh socket 14 composed of a sheet-like material such as orthoplast or another thermoplastic or thermosetting material. The quadrilateral thigh socket 14 includes a ischial weight-bearing shelf 16 having a foam rubber or other soft material sleeve 17 on it. The ischial shelf 16 is about ½ to 2 inches wide, about 1 to 4 inches long, and about ½ to 1 inch deep, appropriate in size for use by a particular patient. The sleeve 17 on the shelf 16 primarily serves to improve the comfort of the patient during use of the assembly 10, an important concern.

The quadrilateral socket 14 of the prosthetic device 12 also includes an underleaved adjustment portion 18 to allow the quadrilateral thigh socket 14 to be fitted to a particular patient. More particularly, when viewed from above, the socket 14 can be considered as having a quadrilateral shape defined by ventral and dorsal walls joined by medial and lateral walls, the underleaved adjustment portion 18 constituting part of any one or two of these walls (and any corner joining them). The quadrilateral shape of the socket 14 and the close sizing allowed by the adjustment portion 18 help prevent rotation of the socket 14 (and thus of the shelf 16 and the prosthetic device 12 itself) with respect to the patient's amputation stump.

For comfort of the patient, the quadrilateral thigh socket 14 can be perforated to allow air flow about the patient's thigh when the prosthetic device 12 is worn. Alternatively, again for the patient's comfort, the socket 14 can be lined with felt or another soft material.

In addition to the socket 14, the temporary weight-bearing prosthetic device 12 includes a support member 20, attached to and extending from the quadrilateral thigh socket 14, for supporting the patient. The support member 20 comprises a pair of uprights, specifically, a medial upright 22 and a lateral upright 24 affixed to the medial and lateral sides of the quadrilateral socket 14, respectively. The medial upright 22 and the lateral upright 24 each include respective upper portions 26 and 28 and lower portions 30 and 32. The upper portions 26 and 28 of the medial and lateral uprights 22 and 24 are each connected to their respective lower portions 30 and 32 by a knee joint 34.

Figure 2:
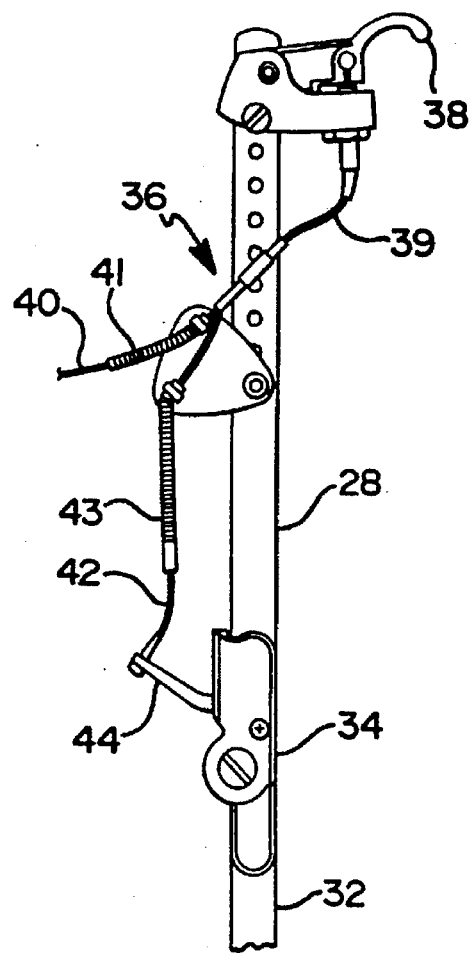
FIG. 2 is a detailed side view of a knee joint and cable release employed in the assembly shown in FIG. 1.

The knee joints 34 and the structure for actuating them are more particularly shown in FIGS. 2 and 4. The knee joints 34 permit pivoting of the lower upright portions 30 and 32 with respect to the upper upright portions 26 and 28 through a range of motion, as indicated in phantom in FIG. 4. The knee joints 34 are shown in FIGS. 2 and 4 in their locked position, in which the lower upright portions 30 and 32 are aligned with the upper upright portions 26 and 28. The knee joints 34 are unlocked from the position shown in FIGS. 2 and 4 by actuation of a manual cable release 36 connected to the uprights 22 and 24.

More particularly, the cable release 36 is actuated by lifting a pull-hook actuator 38 mounted on the upper portion 28 of the lateral upright 24. The pull-hook 38 is connected by a primary cable 39 simultaneously to a medial knee Joint cable 40 contained in an encasement 41, and to a lateral knee joint cable 42 contained in an encasement 43. The ends of the cables 40 and 42 opposite the pull-hook actuator 38 are connected to a bail lever 44 on each of the knee joints 34. As shown in phantom in FIG. 4, a pull on the pull-hook 38 raises the bail lever 44 on each of the knee joints 34 and unlocks the knee joints 34, permitting the lower upright portions 30 and 32 to pivot with respect to the upper upright portions 26 and 28. Preferably, the knee joints automatically lock when the lower upright portions 30 and 32 are returned to alignment with the upper upright portions 26 and 28.

The support member 20 of the temporary prosthetic device 12 includes an endoskeletal shank 46 attached to the lower portions 30 and 32 of the medial and lateral uprights 22 and 24. "Endoskeletal" means that the shank more nearly resembles an internal skeleton, such as that possessed by humans, than to the exoskeleton of an insect or shellfish. This preference for an endoskeletal shank 46, however, does not mean that an exoskeletal shank (such as a hollow, false lower leg) could not be used. The endoskeletal shank 46 includes a medial portion 48 and a lateral portion 50 disposed parallel to and preferably nested inside the lower portions 30 and 32, respectively, of the medial and lateral uprights 22 and 24. The medial and lateral portions 48 and 50 of the endoskeletal shank 46 are joined by a cross-member 49 connected to and extending between them.

The temporary prosthetic device 12 further comprises a means 52 for adjusting the length of the support member 20 to a particular patient. Most conveniently, the adjusting means 52 simultaneously serves to connect the endoskeletal shank 46 to the medial and lateral uprights 22 and 24, and more particularly to connect the endoskeletal shank 46 to the lower portions 30 and 32 of the medial and lateral uprights 22 and 24. For example, the adjusting means 52 can conveniently comprise a plurality of fasteners such as bolts 54 received in two parallel series of holes (not shown) formed in the medial and lateral portions 48 and 50 of the endoskeletal shank 46, and in the lower portions 30 and 32 of the medial and lateral uprights 22 and 24. The adjusting means 52 may instead be formed as any other type of sliding or telescoping connection between the endoskeletal shank 46 and the support member 20, for example, by a slot or slots replacing the series of bolt-receiving holes. The only requirement is that the means 52 be capable of locking in position with sufficient strength to withstand the weight of the patient, yet allow adjustment of the length of the support member 20 while the patient wears the temporary prosthetic device 12. Such an adjustment construction is more significantly convenient to use than the adjustment provided by the solid ankle cushion heel (SACH) assembly employed as a foot-ankle assembly in my earlier application.

The endoskeletal shank 46 further includes a means 58 for adjusting its horizontal width. The horizontal adjusting means 58 is conveniently formed by one or more bolts 62 received in a series of corresponding holes (not shown) in an overlying horizontal part 64 of the medial portion 48 of the shank 46, and a horizontal part 66 of the lateral portion 50 of the endoskeletal shank 46. The horizontal parts 64 and 66 of the medial and lateral portions 48 and 50 of the shank 46 may include slots for receiving the bolts 62, instead of the series of holes. Other adjustment structures may also be convenient.

A ground-engaging member is adjustably affixed directly to the endoskeletal shank 46, distal to the quadrilateral socket 14. The member can be a simple walking tip composed, for example, of rubber. Preferably, however, the member is an artificial foot 68. Conveniently, the foot 68 can be mounted to either of the horizontal parts 64 or 66 of the medial and lateral portions 48 and 50 of the shank 46, and is preferably affixed to them by the same bolts 62 which fix and locate the horizontal parts 64 and 66 with respect to one another. The artificial foot 68 is also adjustable in position both dorsally and ventrally with respect to the endoskeletal shank 46. For any particular patient, selection of the appropriate location of the artificial foot 68 with respect to the shank 46, as well as vertical adjustment of the shank 46 with respect to the medial and lateral uprights 22 and 24, will be well within the scope of the skill of anyone in this field, in light of the instant specification.

Advantageously, the temporary prosthetic device 12 includes a suspension means 74 for supporting the device 12 on a patient. The support means 74 can, for example, be a modified Silesian band of the type shown in FIG. 1, including a torso or waist strap 75 fitted about the patient.

The temporary prosthetic device 12 is advantageously used in such a manner so that the entire weight of the patient is supported by the ischial weight-bearing shelf 16, rather than by any part of the patient's amputation stump. This advantage is achieved by employing the temporary prosthetic device 12 in combination with an independent stump dressing 76 which is dimensioned to leave the portion of the patient's gluteus maximus over the ischial tuberosity (that is, the gluteal crease) free for engagement with and support by the ischial shelf 16 of the temporary prosthetic device 12.

The dressing 76 is adapted for immediate post-operative placement around the patient's amputation stump, and includes a means 77 for providing mild uniform circumferential compression to the amputation stump and suppressing edema of the stump. The dressing 76 in its simplest form includes a pad 78 (such as foam rubber) continuously disposed about the stump; the circumferential compression means 77 then comprises at least one and preferably a plurality of adjustable bands or straps 79 disposed about the pad 78. The straps are about 1 to 2 inches wide and are faced, for example, with mating portions of a hook and loop-type fastener, such as VELCRO (a trademark of Velcro Corporation), for ease of securement and release. In this manner, the dressing 76 is removable from the stump without injury to the stump, replaceable on the stump, and size-adjustable to either fit different patients or to fit a particular patient's stump as the stump reduces in size during healing.

Figure 7:
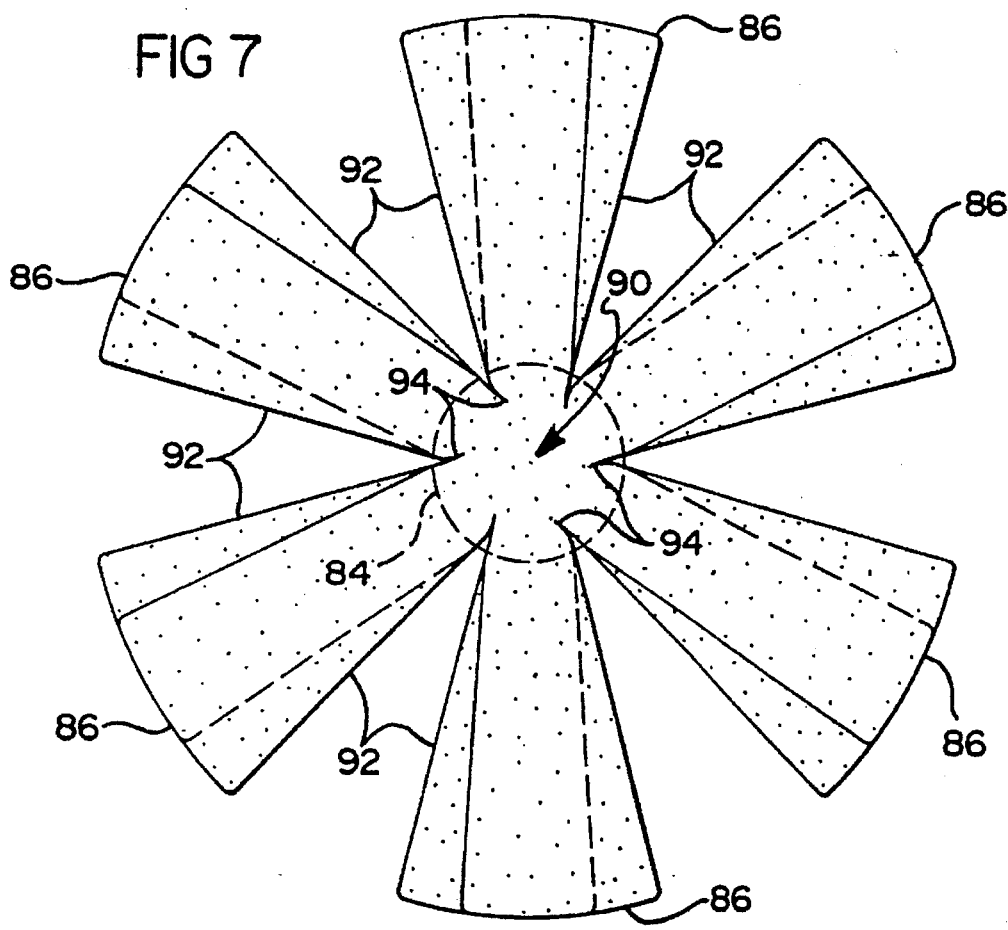
FIG. 7 is a top view of the dressing pad shown in FIG. 6, partly unfolded to more clearly show its construction.
Figure 6:
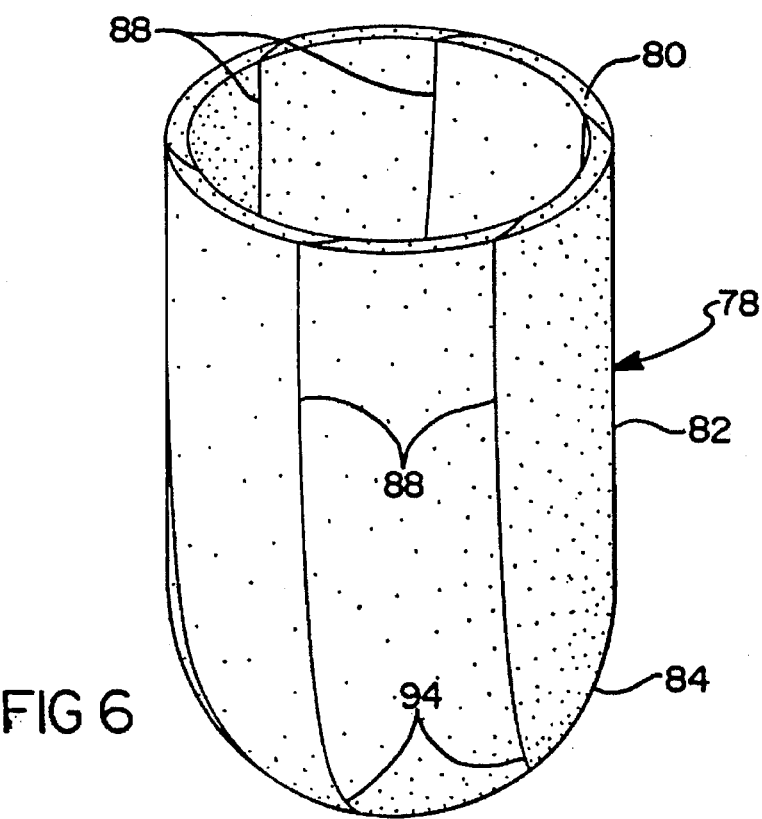
FIG. 6 is a perspective view of a pad incorporated in the prosthetic assembly of FIGS. 1 and 5.

The pad 78 of the dressing 76 is more clearly shown in FIGS. 6 and 7. The pad 78 includes a generally cylindrical hollow body 82 having an open upper end 80, and a generally hemispherical closed end 84 opposite the upper end 80. The pad 78 is configured as a plurality of longitudinally extending petals 86 formed by a plurality of cuts 88 longitudinally extending through the pad body 82 and through part of the closed pad end 84. The cuts 88 are preferably angled with respect to the axis 90 of the pad body 82 so that the edges 92 of the pedals 86 are tapered and lie over one another when the pad 78 is positioned for use, in the configuration shown in FIG. 6. The cuts 88 are preferably curved or arcuate, so as to provide similar overlying edges 94 at the closed end 84 of the pad body 82. In this manner, localized pressure areas from the pad can be avoided during use. It is preferred, however, that the cuts 88 do not extend to the axis 96 of the pad body 82, so that the pad 78 remains composed as a single piece.

Figure 8:
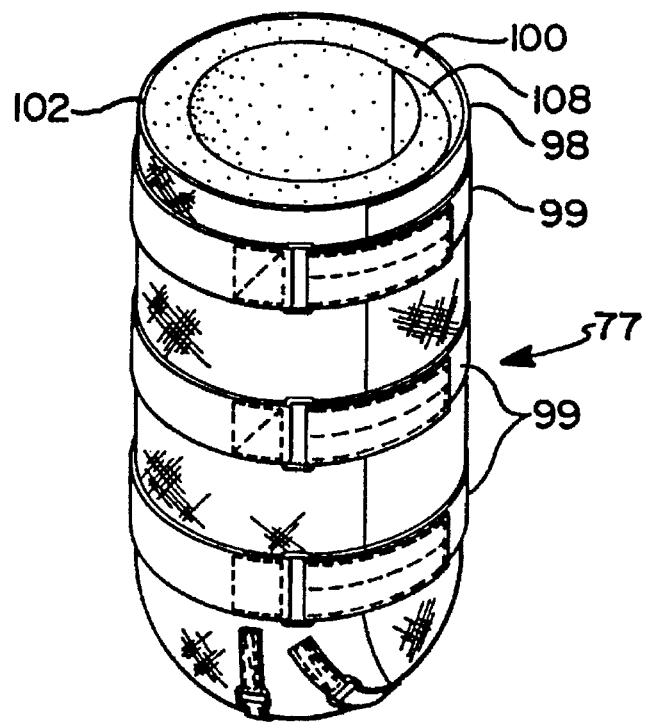
FIG. 8 is a perspective view of an alternative dressing for incorporation in the prosthetic assembly of the present invention.
Figure 9:
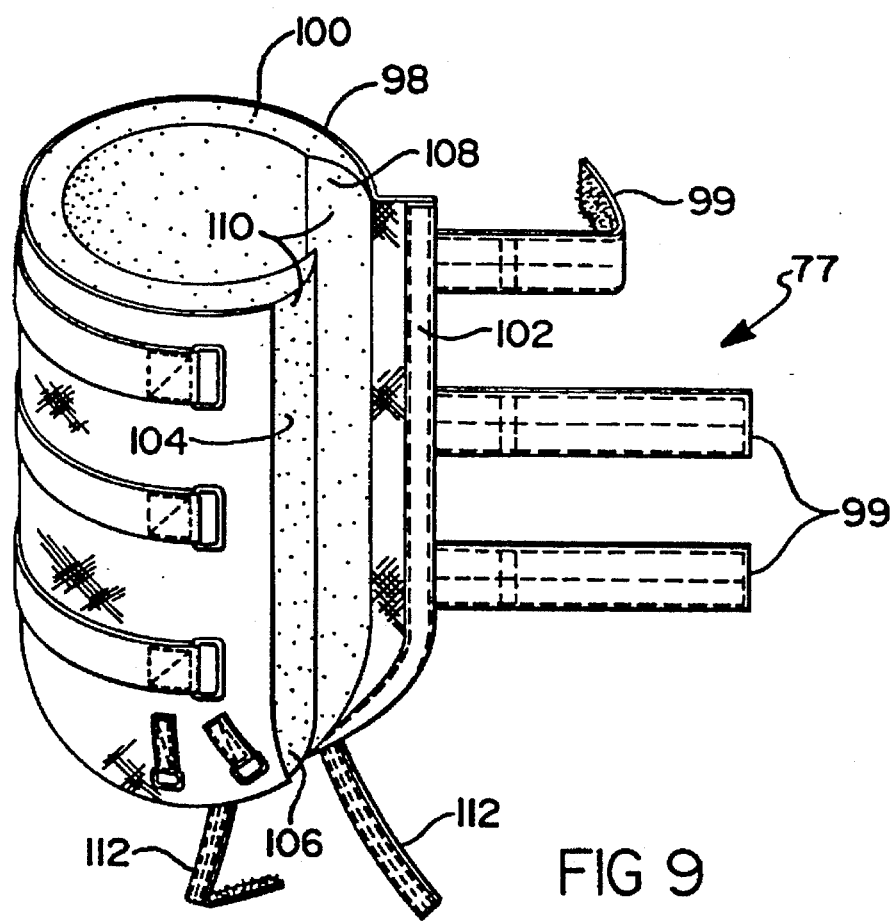
FIG. 9 is a perspective view similar to FIG. 8, showing the dressing opened for application or removal.

Of course, more complex constructions can be used for, or in conjunction with, the circumferential compressing means 77 of the dressing of the present invention. The dressing 98 shown in FIGS. 8 and 9, for example, is similar to that shown in FIGS. 1, 6 and 7, in that it includes a circumferential compressing means 77 formed as a plurality of VELCRO-faced straps 99, for compressing a pad 100 about the patient's stump. The dressing 98, however, additionally comprises a durable fabric cover 102 positioned over the pad 100 and preferably adhered to it with a light adhesive. The straps 99 are affixed to the cover 102, rather than to the pad 100.

The pad 100 is similar to the pad 78 in that it includes a generally cylindrical hollow body 104 and hemispherical closed lower end 106. The pad 100, however, possesses only a single longitudinally extending cut 108 through the cylindrical body 104 and the hemispherical end 106. The cut 108 is angled with respect to the axis of the cylindrical body 104 to provide overlapping tapered edges 110 on the body 104, serving the same purpose as the tapers on the edges 94 of the pad 78. However, the longitudinally extending cut 108 of the pad 100 passes through the axis of the pad at the hemispherical end 106. Further, the cut 108 is angled with respect to the surface of the pad 100 at the hemispherical end 106, and preferably somewhat sinuous in shape at the pad end 106, so that (unlike the tapered edges 94 of the pad 78) the tapered edges 110 extend fully to, and overlap at, the body axis.

Figure 10:
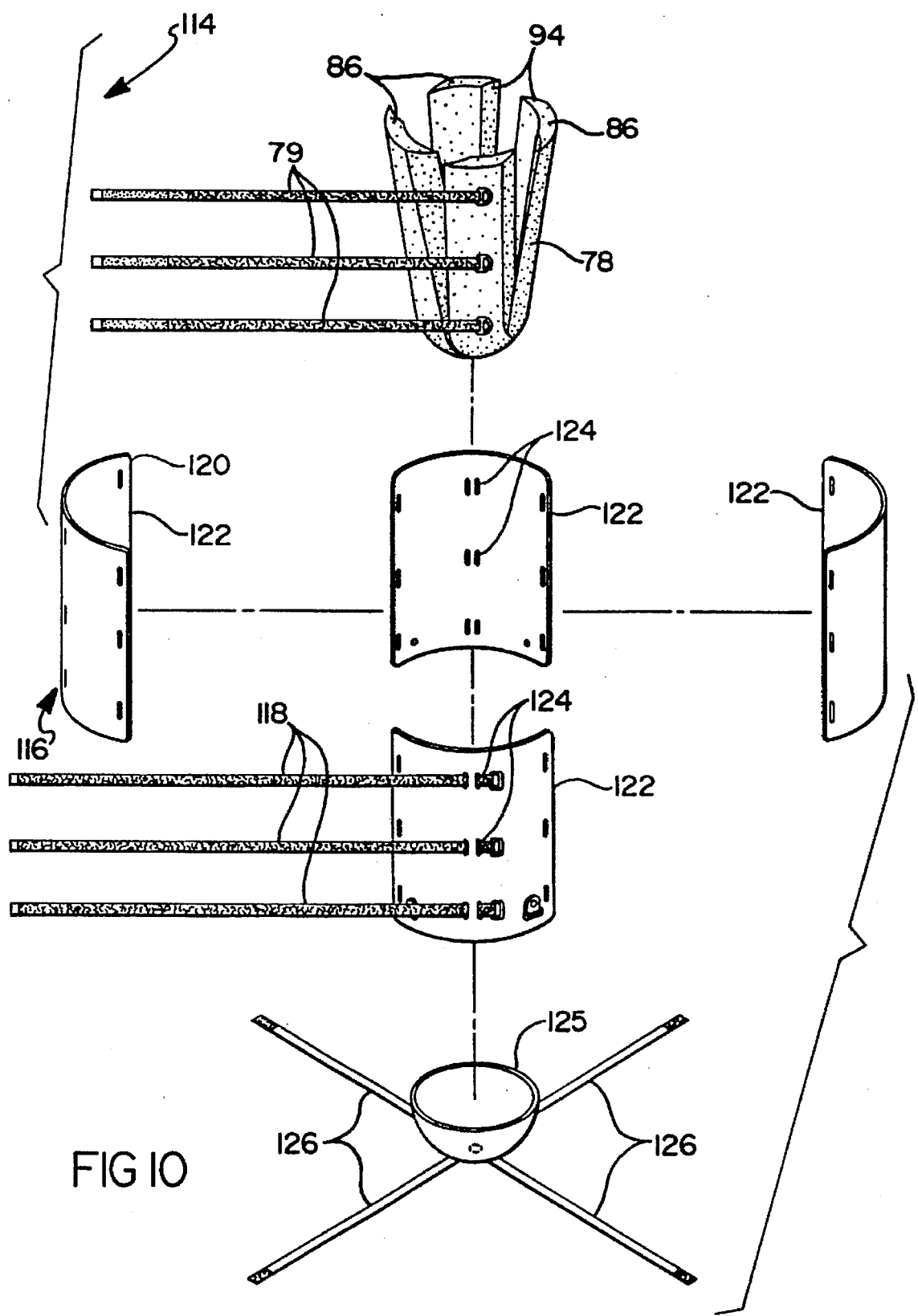
FIG. 10 is fragmentary view of another alternative dressing for incorporation in the prosthetic assembly of the present invention.
Figure 11:
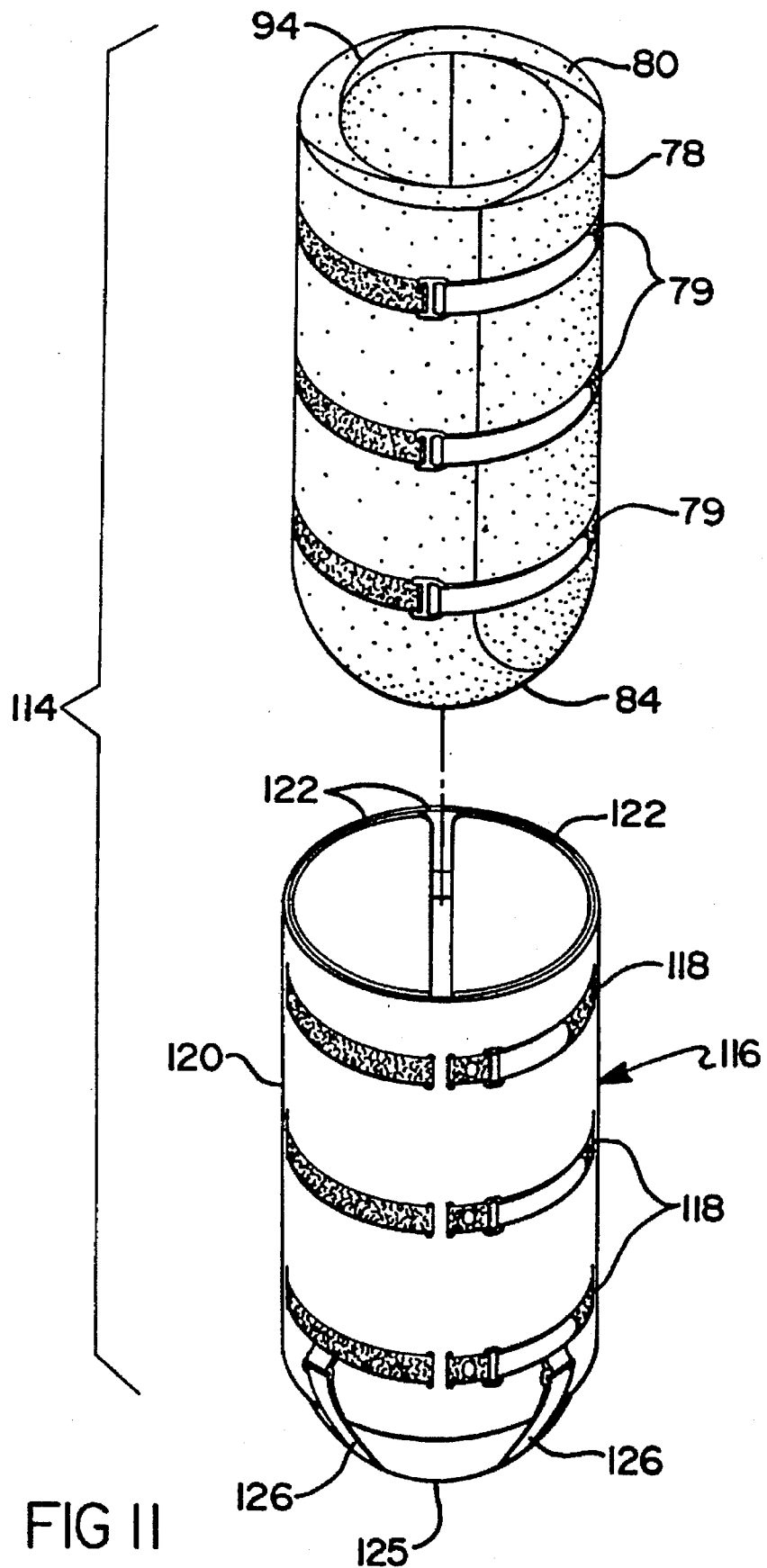
FIG. 11 is a perspective view of the dressing of FIG. 10, shown assembled.

This construction not only eases the introduction of the dressing 98 onto the patient's stump, it also permits an additional compressive force to be applied by at least one and preferably two supplemental end straps 112 on the hemispherical pad end 106, lying across the cut 108. The end straps 112 aid in preventing or reducing edema of the end of the stump ("mushrooming") when the circumference of the stump is under the compressive force of the circumferential compression means 77, that is, the straps 99. Conveniently, the straps 99 and 112 can be sewn or otherwise affixed to the fabric cover 102 along a substantial part of their lengths, the VELCRO-faced portions then being free of connection to the cover 102, allowing adjustment of the compressive force they apply. Also conveniently, the cover 102 overlies the cut 108, both for cosmesis, and to provide a barrier to the intrusion of foreign material between the pad edges A dressing useful in the practice of the present invention need not only be soft or non-rigid, however. For example, as shown in FIGS. 10 and 11, a dressing 114 in accordance with the present invention can comprise a rigid but adjustable portion 116 positioned between an appropriate pad (such as the pad 78, with or without the straps 79) and at least one, and preferably several, VELCRO-faced straps 118. The rigid portion 116 and the straps 118 thereby compose a circumferential compressing means equivalent to the compressing means 77 of the dressing 76. In this construction, the straps 79 can serve as part of the compressing means, but preferably function merely to hold the petals 86 in place during application of the dressing 114 on the stump. Other means for holding the petals 86 together at this time can be used, for example, a light adhesive placed on the overlapping pad edges 94.

The rigid portion 116 of the dressing 114 first comprises a hollow cylindrical shell 120 composed of a plurality of shell sections 122 each having slots 124 for receiving the straps 118 therethrough. The straps 118 are attached to one of the shell sections 122 by any convenient means, for example, by riveting. The cylindrical shell 120 can then be adjusted in size by loosening or tightening the straps 118, and in this way achieve adjustment of the circumferential pressure applied to the stump.

The rigid portion 116 of the dressing 114 also comprises a hemispherical end cap 125 received within the cylindrical shell 120, in abutment against the closed end 84 of the pad 78. The end cap 125 is attached to the cylindrical shell 120 by a plurality of VELCRO-faced straps 126; tightening or loosening the straps 126 positions the end cap 125 with respect to the cylindrical shell 120, and thereby varies the compressive force applied to the end 84 of the pad, and through it, to the end of the patient's stump. It should be evident that the end cap 125 thus serves the same purpose as the supplemental end straps 112 of the covered soft dressing 98, in that the end cap 125 serves to reduce or eliminate edema of the end of the amputation stump, when the stump is circumferentially compressed by the compressing means 77.

As more particularly shown in FIG. 11, in the use of the dressing 114, the pad 78 is first applied over the stump, with due care taken to avoid localized pressure spots, and the straps 79 tightened somewhat, but not to the degree necessary to provide the full desired amount of circumferential compression to the patient's stump. The shell sections 122 and the end cap 125 are then loosely assembled, and slid over the pad 78. The straps 118 and 126 are then tightened to an appropriate degree to yield the application of proper pressure to the amputation stump, both circumferentially and at its end.

Two other preferred embodiments for a rigid stump dressing are disclosed in my parent U.S. patent application Ser. No. 408,884, which is incorporated by reference herein. Both embodiments can be described with reference to the single dressing shown in FIGS. 12 and 13. In a first of these embodiments, the circumferential compressing means 77 of the dressing includes a substantially stump-shaped rigid cast portion 170 for placement around the stump. The cast portion 170 is open-ended at the top and shaped to enclose and to secure around the stump at its bottom so as to apply mild compression for suppressing edema of the stump. The cast portion 170 has four interconnected but separable shell sections 180, 182, 184 and 186 with vertical slits or separations 172,174, 176 and 178 extending from one end of the cast portion 170 to the other end of the cast portion 170. The vertical separations 172, 174, 176 and 178 are substantially located at 0°, 90°, 180°, and 270° of the circumference of the cast portion 170. The cast portion has locking means (such as self-adhering VELCRO-faced belts 212, 214 and 216) at two of the opposing vertical separations 172 and 176, so that the cast portion can be separated into two pieces for removal and physiological inspection of the stump, and rejoined and locked onto the patient's stump thereafter. The cast portion also has a sizing means (such as slots 188, 190, 192 and 194 receiving therein fasteners 204,206 and 210) between the other two opposing vertical separations 174 and 178, so that the cast portion 170 can be adjusted in size circumferentially.

A second embodiment of my prior rigid dressing similarly includes a substantially stump-shaped rigid cast portion 170 as the compressing means 77, the cast portion 170 being open-ended at its top and shaped to enclose and secure around the stump at its bottom, so as to apply a mild compression for suppressing edema of the stump. The cast portion 170 has two separatable vertical half shells, each half shell having two vertical separatable overlapping sections 180 and 182, or 184 and 186. The overlapping sections 180, 182, 184 and 186 are slidably adjustable for adaptation to different sized stumps. The cast portion has a sizing means (such as the sizing means mentioned above) for adjusting the cast portion 170 in circumferential size and for holding the overlapping sections 180 and 182, or 184 and 186, together. The cast portion further includes locking means (such as the locking means disclosed above) for securing the two half shells together around the amputation stump.

Each of these rigid cast constructions optionally includes a soft and compressible cast lining (such as the pad 78 described above) to ensure the uniform application of pressure to the stump. The lining is preferably composed of foam rubber about ½ to 1 inch thick. The lining preferably includes a plurality of connected lobes or petals extending parallel to the cast shells or cast sections, having overlapping but tapered edges. In this way, bulging of the lining is avoided during compression. Bulging, of course, can adversely cause areas of localized pressure, interfering with circulation and impairing healing of the amputation stump.

The rigid cast portions of any of these constructions can be composed of a thermoplastic or thermosetting material, or a glass fiber-resin composite. Advantageously, because their cast portions are adjustable in circumference, the rigid dressings can be stocked for a wide variety of patents from only a few sizes. Their rigid cast portions can be manufactured with a length appropriate to below-knee and knee disarticulation applications, and then cut to a shorter length at the location of use to adapt the dressing to above-knee applications. Moreover, the rigid cast portions are preferably constructed of material subject to ready sterilization, making re-use possible. These advantages may, in some cases, outweigh the additional expense encountered over the use of the disclosed soft dressings.

The non-rigid dressings disclosed earlier are inherently less adjustable to patient size than are the rigid dressings, so that a greater but still limited number of lengths and circumferences need be stocked in order to provide dressings for a variety of patients. Because of the low cost of manufacture of the soft dressings, however, it is still inexpensive to stock an adequate number of varieties.

Other soft or rigid dressing constructions useful in conjunction with the temporary prosthetic device 12 will be evident to those skilled in the art, in light of the instant specification. The important point of the dressing is that it does not interfere with the engagement of the patient's gluteal cleft with the ischial weight-bearing shelf 16 of the temporary prosthetic device 12.

The embodiment of the prosthetic assembly 10 shown in FIG. 1 is particularly adapted for use by a patient who has been subjected to an above knee amputation. When fitted to the patient, the upper end 80 of the dressing 76 will lie below the portion of the patient's gluteus maximus over the ischial tuberosity. When the patient's stump is then inserted into the temporary prosthetic device 12 (through the quadrilateral socket 14 and between the upper portions 26 and 28 of the medial and lateral uprights 22 and 24), the weight of the patient will be borne on the ischial weight-bearing shelf 16, and no weight will be placed upon the dressing 76 or the patient's stump. The means 52 for adjusting the length of the support member 20, and the means 58 for adjusting the horizontal length of the endoskeletal shank 46, readily allow adjustment of the position of the artificial foot 68 with respect to the shank 46. The temporary prosthetic device 12 is thus easily fitted to any particular patient.

A modified version of the prosthetic assembly 10 shown in FIG. 1, particularly adapted for a patient having a below knee amputation, is shown in FIG. 5. Like-numbered parts are shared between the two views, so that the same elements shown in FIGS. 5 and 1 need not be described in detail again. However, in contrast to the device 10 as shown in FIG. 1, the device shown in FIG. 5 includes a wider endoskeletal shank 46, and includes lower portions 30 and 32 of the medial and lateral uprights 22 and 24 which are spaced further apart, allowing introduction of the stump and dressing 76 therebetween.

In order to avoid undesirable movement of the dressing and stump extremity with respect to the temporary prosthetic device 12 (so-called "flopping"), two further modifications to the device 12 are made, in contrast to the embodiments shown in FIG. 1. First, a knee pad 70 is detachably and adjustably secured on the medial and lateral uprights 22 and 24 in the area of the knee joints 34. The knee pad 70 is a generally rectangular piece of an impact absorbing material, for example, a fabric or rubber pad. The pad 70 protects the patient's knee from abrasion or bruising during use of the prosthetic assembly 10. Adjustment of the knee pad 70 is most easily obtained by a pair of straps 71, including hook and loop-type fasteners, adjustably and detachably secured to the upper portions 26 and 28 and the lower portions 30 and 32 of the medial and lateral uprights 22 and 24.

Second, a curved back plate 72 (concave towards the ventral direction or front of the patient) is secured to and positioned between the lower portions 30 and 32 of the medial and lateral uprights 22 and 24. The back plate 72 limits dorsal or rearward movement of the dressing 76 and the enclosed stump. The curved plate 72 is essentially rigid and can be composed of either a synthetic material or metal.

Use of the prosthetic assembly 10 according to the present invention is straightforward, and advantageously occurs for the first time within a few hours or days after the amputation operation. To use the prosthetic assembly of this invention, a freshly-sutured limb is first bandaged and covered with thin sterile stump socks, as desired. Next, the compressible lining (such as the pad 78) is applied, for example, by placing the center of the lining on the end of the stump, and the petals or other pieces of the lining are folded onto the stump. The petals may be held in place temporarily by application of a light, non-permanent adhesive. If used, the rigid cast portion, which has been adjusted to fit the patient by adjusting the adjustment means while the locking means are fastened closed, is applied over the compressible lining. Alternatively, the circumferential comprising means 77 (for example, the straps 79) about the lining are secured so as to apply an appropriate and uniform amount of pressure to the amputation stump. The dressing, by providing uniform, controlled compression on the stump, reduces the swelling of the stump either arising post-operatively or caused during dependent positions while standing and walking.

Next, an appropriately-sized proximal contact lower limb prosthetic device 12 is fitted on the patient about the rigid dressing. The prosthesis can be adjusted in size vertically and horizontally after being fitted on the patient, so that the prosthesis does not conflict with the dressing already in place.

Thus, it should readily be apparent that the present invention provides an immediate post-operative ischial weight-bearing lower limb prosthetic assembly which fully meets the objects and achieves the advantages set forth above. Most importantly, the prosthetic assembly is readily adjustable to any particular patient, yet is subject to reuse without difficulty. Moreover, the assembly is adapted to make it as easy for the patient to use as possible, avoiding the previously encountered pain both in removal and reconstruction of the dressing, and in bearing the weight of the patient ischially, rather than on the stump itself. A device which is easier to use is more likely to be used, and more likely to benefit the patient.

The traditional drawbacks of the rigid cast dressing are avoided because the wound is open for inspection, and interference with the wound healing is avoided. The prosthetic assembly of the present invention may be used in rural hospitals where expert prosthetists are not available, and may be used until a definitive prosthetic fitting has taken place. Physical and psychological benefits to the patient are realized when the patient is able to walk within the first few days after the amputation operation, generally on the first day.

INDUSTRIAL APPLICABILITY

The present invention provides an immediate post-operative dressing, and a lower limb prosthetic assembly incorporating the same, for patients subjected to above-knee amputations, knee disarticulartions, or below-knee amputations. The dressing and assembly can easily be fitted to a variety of patients, yet are subject to re-use without difficulty, and advantageously permit patient ambulation (without pain to the amputation stump) as early as a few hours after the amputation operation.

While the invention has been described in conjunction with the specific embodiments thereof, it is evident that many alternatives, modifications and variations will be apparent to those skilled in the art in light of the foregoing description. Accordingly, Applicant intends to embrace all such alternatives, modifications and variations as may fall within the spirit and scope of the appended claims.

What is claimed is:

1. A lower limb prosthetic assembly for immediate post-operative amputation applications, comprising:
   a temporary weight-bearing prosthetic device including:
   (a) an open-ended quadrilateral thigh socket having an ischial weight-bearing shelf for supporting the patient without contact to the amputation wound;
   (b) a support member attached to and extending from the quadrilateral thigh socket for supporting the patient; and
   (c) means for adjusting the length of the support member to a particular patient; and
   an independent, removable, replaceable, size-adjustable dressing configured for immediate post-operative placement around the patient's amputation stump, and being insertable in the thigh socket of the prosthetic device when in place on the stump, the dressing having means, independent of the prosthetic device, for providing uniform circumferential compression to the amputation stump and for suppressing edema of the stump, the dressing being dimensioned to leave the portion of the patient's gluteus maximus over the ischial tuberosity free for engagement with and support by the ischial shelf of the temporary prosthetic device.

2. The prosthetic assembly of claim 1, wherein the support member includes a medial upright and a lateral upright, each of the medial and lateral uprights including an upper and a lower portion, and a knee joint connecting the upper and lower portion; and an endoskeletal shank attached to the lower portions of the medial and lateral uprights.

3. The prosthetic assembly of claim 2, wherein the knee joints include locks, and the prosthetic assembly further comprises a manually-operable cable release for the knee locks.

4. The prosthetic assembly of claim 2, wherein the means for adjusting the length of the support member connects the endoskeletal shank to the medial and lateral uprights.

5. The prosthetic assembly of claim 2, wherein the support member further comprises a foot assembly affixed to the endoskeletal shank.

6. The prosthetic assembly of claim 2, wherein the endoskeletal shank is substantially U-shaped and possesses medial and lateral vertical portions.

7. The prosthetic assembly of claim 6, wherein the shank further comprises means for adjusting the horizontal width of the shank.

8. The prosthetic assembly of claim 7, wherein the horizontal adjusting means comprises a pair of overlying horizontal parts extending from the medial and lateral portions of the shank, and means adjustably fastening the horizontal parts to one another.

9. The prosthetic assembly of claim 8, further comprising a foot assembly adjustably affixed to one of the horizontal parts of the endoskeletal shank.

10. The prosthetic assembly of claim 1, further comprising a padded sleeve on the ischial shelf of the quadrilateral thigh socket.

11. The prosthetic assembly of claim 2, wherein the endoskeletal shank includes medial and lateral shank portions.

12. The prosthetic assembly of claim 11, further comprising a back affixed to the medial and lateral endoskeletal shank portions, restricting dorsal movement of the dressing and enclosed stump.

13. The prosthetic assembly of claim 11, further comprising a ventral knee pad connected to the medial and lateral uprights adjacent to the knee joints.

14. The prosthetic assembly of claim 1, wherein the dressing is rigid and comprises a substantially stump-shaped rigid cast portion for placement around the stump, the cast portion being open-ended at the top and shaped to enclose and secure around the stump at its bottom so as to apply compression for suppressing edema of the stump, the cast portion having four interconnecting shell sections with vertical separations extending from one end of the cast portion to the other end of the cast portion, wherein the vertical separations are substantially located at 0°, 90°, 180°, and 270° of the circumference of the cast portion, the cast portion having (a) locking means at two of the opposing vertical separations so that the cast portion can be separated into two pieces for removal and inspection of the physiological status of the stump and rejoined and locked onto the patient's stump; and (b) sizing means between the other two opposing vertical separations so that said cast portion can be adjusted in size circumferentially.

15. The prosthetic assembly of claim 1, wherein the dressing is rigid and comprises a substantially stump-shaped rigid cast portion for placement around the patient's stump, the cast portion being open-ended at its top and shaped to enclose and secure around the stump at its bottom, so as to apply compression for suppressing edema of the stump, the cast portion having (a) two separatable vertical half shells wherein each half shell has two vertically-separatable overlapping sections including an outside overlapping section and an inside overlapping section, the overlapping sections being slidably adjustable for adaptation to different sized stumps; (b) sizing means on the cast portion for adjusting the cast portion in circumferential size and for holding the overlapping sections together; and (c) locking means for securing the two half shells together around the amputation stump.

16. The prosthetic assembly of claim 1, wherein the dressing comprises a pad, and the compression means is disposed about the pad for compressing the pad against the patient's amputation stump.

17. The prosthetic assembly of claim 16, wherein the compression means comprises a multipiece rigid shell having (a) means for adjusting the circumference of the dressing by adjusting the positions of the shell pieces with respect to one another, and (b) means for splitting and reclosing the dressing by separating one or more of the shell pieces from the others.

18. The prosthetic assembly of claim 16, wherein the compression means comprises a hollow cylindrical shell of adjustable circumference positioned about the pad.

19. The prosthetic assembly of claim 16, wherein the compression means comprises at least one releasable strap circumferentially disposed about and secured about the pad.

20. The prosthetic assembly of claim 19, wherein the pad includes a generally cylindrical body and a hemispherical closed end, the pad having a plurality of laterally tapered, longitudinally extending petals formed by longitudinally extending cuts through the body and through part of the closed end.

21. The prosthetic assembly of claim 19, wherein the compression means further comprises a rigid shell positioned between the pad and the circumferentially disposed at least one strap.

22. The prosthetic assembly of claim 21, wherein the shell is configured as a hollow cylinder having a plurality of separable and longitudinally extending pieces.

23. The prosthetic assembly of claim 22, wherein the dressing further comprises (a) an end cap received over the pad in the cylinder, and (b) means for urging the end cap towards the end of the stump and compressing the pad against the end of the stump.

24. The prosthetic assembly of claim 19, wherein the compression means further comprises a fabric cover positioned between the pad and the circumferentially disposed at least one strap.

25. The prosthetic assembly of claim 24, wherein the pad includes a generally cylindrical body and a hemispherical end, the body and end being longitudinally split by a longitudinally extending cut through the body and through part of the hemispherical end, the cut extending in the hemispherical end to at least the axis of the cylindrical body.

26. The prosthetic assembly of claim 25, wherein the dressing further comprises at least one end strap secured to the fabric cover, crossing the cut in the hemispherical end of the pad.

27. A dressing for immediate post-operative lower limb amputation applications, comprising an independent, removable, replaceable, size-adjustable, non-inflatable dressing configured for immediate post-operative placement around a patient's amputation stump and subsequent insertion into a prosthetic device, the dressing comprising means, independent of the prosthetic device, for providing uniform circumferential compression to the amputation stump and for suppressing edema of the stump, the dressing being dimensioned to leave the portion of the patient's gluteus maximus over the ischial tuberosity free to bear the full weight of the patient.

28. The dressing of claim 27, wherein the dressing comprises a pad, and the compression means is disposed about the pad for compressing the pad against the patient's amputation stump.

29. The dressing of claim 28, wherein the compression means comprises a multipiece rigid shell having (a) means for adjusting the circumference of the dressing by adjusting the positions of the shell pieces with respect to one another, and (b) means for splitting and reclosing the dressing by separating one or more of the shell pieces from the others.

30. The dressing of claim 28, wherein the compression means comprises a hollow cylindrical shell of adjustable circumference positioned about the pad.

31. The dressing of claim 28, wherein the compression means comprises at least one releasable strap circumferentially disposed about and secured about the pad.

32. The dressing of claim 31, wherein the pad includes a generally cylindrical body and a hemispherical closed end, the pad having a plurality of laterally tapered, longitudinally extending petals formed by longitudinally extending cuts through the body and through part of the closed end.

33. The dressing of claim 31, wherein the compression means further comprises a rigid shell positioned between the pad and the circumferentially disposed at least one strap.

34. The dressing of claim 33, wherein the shell is configured as a hollow cylinder having a plurality of separable and longitudinally extending pieces.

35. The dressing of claim 34, wherein the dressing further comprises (a) an end cap received over the pad in the cylinder, and (b) means for urging the end cap towards the end of the stump and compressing the pad against the end of the stump.

36. The dressing of claim 31, wherein the compression means further comprises a fabric cover positioned between the pad and the circumferentially disposed at least one strap.

37. The dressing of claim 36, wherein the pad includes a generally cylindrical body and a hemispherical end, the body and end being longitudinally split by a longitudinally extending cut through the body and through part of the hemispherical end, the cut extending in the hemispherical end to at least the axis of the cylindrical body.

38. The dressing of claim 37, wherein the dressing further comprises at least one end strap secured to the fabric cover, crossing the cut in the hemispherical end of the pad.

39. The dressing of claim 28, wherein the pad comprises a non-inflatable, soft, resilient and compressible material.

40. The dressing of claim 27, wherein the dressing is adapted to cover the end of the amputation stump and the compression means includes means for applying terminal compression to the end of the amputation stump.

41. A lower limb prosthetic device for post operative amputation or early fitting applications, comprising:
an open-ended thigh socket having an ischial weight-bearing shelf for supporting the patient without contact to the amputation wound, said thigh socket defining a longitudinal axis and including a longitudinal opening, and said thigh socket including means for adjusting the opening for close circumferential size fitting of the thigh socket to a broad range of residual limb sizes and for preventing rotation of the thigh socket on a respective residual limb; and
a prosthetic support member attached to and extending from the thigh socket for supporting the patient, wherein the support member includes a medial upright and a lateral upright, each of the medial and lateral uprights including: an upper portion; a knee joint; a lower portion connected to the upper portion by the knee joint, the upper portions having respective upper ends attached to the thigh socket and the lower portions having respective lower ends; and first adjusting means for adjusting a length of each of the lower portions.

42. The prosthetic device according to claim 41, wherein the adjusting means comprises an underleaved adjustment portion that permits the thigh socket to be adjusted to a particular patient.

43. The prosthetic device according to claim 42, wherein the thigh socket comprises a quadrilateral thigh socket.

44. The prosthetic device of claim 41, wherein the support member further comprises second adjusting means for adjustably fixing the lower ends of the lower portions of the medial and lateral uprights relative to one another for adjusting a spacing between the uprights.

45. The prosthetic device according to claim 44, wherein the knee joint comprises one of the bail lock and drop lock type.

46. A soft dressing for post operative amputation applications comprising:
a soft dressing configured for circumferentially positioning about an amputation stump and subsequently inserting into a prosthetic divide, said dressing including means for providing circumferential protection to the amputation stump; said dressing being a non-inflatable, soft, resilient, compressible material; and said dressing including means, independent of the prosthetic device, for enabling circumferential size adjustability of said dressing to cover the amputation stump and for applying a uniform, circumferential compression to the amputation stump.

47. The dressing according to claim 46, wherein the dressing is an integral one piece design.

48. The dressing of claim 46, wherein the dressing is adapted to cover the end of the amputation stump and includes means for applying a terminal compression to the end of the stump.

49. A lower limb prosthetic device for post operative amputation or early fitting applications, comprising:

an open-ended circumferentially adjustable thigh socket having an ischial weight-bearing shelf for supporting the patient without contact to the amputation wound and said thigh socket defining a longitudinal axis and including a longitudinal opening;

a support member attached to and extending from the thigh socket for supporting the patient; and a soft dressing adapted for circumferentially positioning about an amputation stump for insertion in the thigh socket when in place on the stump, said dressing including means for providing circumferential protection to the amputation stump; said dressing being a non-inflatable, soft, resilient, compressible material size adjustably dimensioned to cover the amputation stump and including means, independent of the thigh socket, for applying a uniform circumferential compression to the amputation stump.

50. The prosthetic device of claim 49, wherein the dressing is adapted to cover the end of the amputation stump and the compression means includes means for applying terminal compression to the end of the amputation stump.

51. The prosthetic assembly of claim 16, wherein the pad comprises a non-inflatable, soft, resilient and compressible material.

52. The prosthetic assembly of claim 1, wherein the dressing is adapted to cover the end of the amputation stump and the compression means includes means for applying terminal compression to the end of the amputation stump.

* * * * *